Figure 1:
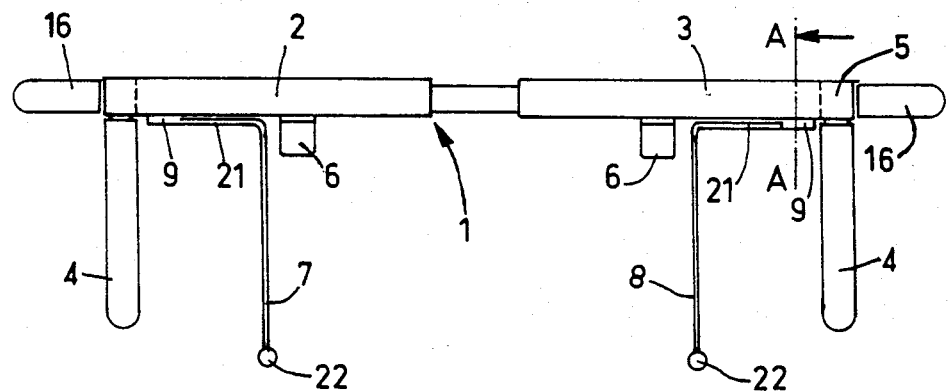

United States Patent [19]

Cogez

[11] Patent Number: 4,494,836
[45] Date of Patent: Jan. 22, 1985

[54] DEVICE FOR DETERMINING AND MEASURING MONOCULAR PUPILLARY DEVIATIONS IN A PATIENT'S EYES

[75] Inventor: Jean Cogez, Paris, France

[73] Assignee: Essilor International, Creteil, France

[21] Appl. No.: 368,014

[22] Filed: Apr. 13, 1982

[30] Foreign Application Priority Data

Apr. 29, 1981 [FR] France .................... 81 08 558

[51] Int. Cl.³ .............................................. A61B 3/10
[52] U.S. Cl. ...................................... 351/204; 33/200
[58] Field of Search ........................... 351/204; 33/200

[56] References Cited

U.S. PATENT DOCUMENTS 2,596,264  5/1952  Macbeth ................. 351/204
4,252,419  2/1981  Padula et al. .......... 351/204

FOREIGN PATENT DOCUMENTS 626277  10/1961  Italy ..................... 351/204

Primary Examiner—Rodney B. Bovernick
Attorney, Agent, or Firm—Burgess, Ryan & Wayne

[57] ABSTRACT

The invention provides a simple and accurate device for determining and/or measuring monocular pupillary deviations in a patient's eyes that is, the distance in normal distant or near sight between the center of the pupil of each eye and the plane of virtual symmetry of the patient's face. The device comprises a cross bar carrying two adjustable reticles; the bar is formed of two casings which can move telescopically in relation to each other and each of which contains a runner capable of moving inside it under the control of an outside regulating knob and connected to a removable reticle-holder pin, each said telescopic casing comprising a downward-pointing arm held against the corresponding inside or outside surface of one of the arms of the spectacle frame, by at least one spring exerting force on each casing, the aforesaid device being characterized by the fact that each casing comprises an internal extension enabling the two casings to fit telescopically inside each other and which includes a supporting device for one end of a compression spring so that the force of the spring causes the casings to move away from each other and presses the downward arms against the inside surface of the spectacle arms.

6 Claims, 7 Drawing Figures

DEVICE FOR DETERMINING AND MEASURING MONOCULAR PUPILLARY DEVIATIONS IN A PATIENT'S EYES

This invention concerns a device for determining and/or measuring monocular pupillary deviations in a patient's eyes, i.e. the distance in normal distant or near sight between the centre of the pupil of each eye and the plane of virtual symmetry of the patient's face, corresponding in practice to the plane of symmetry of the spectacle frame worn by the patient.

Many appliances already exist to measure these pupillary deviations. Some extremely simple ones are in the form of a ruler, but these are not accurate enough to allow proper centring of the lenses in the frame, particularly in the case of progressively variable-focus lenses, which require high-precision fitting. Other devices, such as the corneal-reflection pupillometer described in French patent No. 1 506 352 of Aug. 4, 1966, are very accurate, but rather expensive.

It is also possible to use a photographic mensurator, which provides a straightforward way of determining the position of the centre of the pupil of each eye in relation to the inside circumference of the corresponding frame aperture. However, this type of photograph shows only one kind of pupillary deviations in either near sight or far sight. This is not enough to allow a progressively variable-focus lens to be centred and angled precisely on an apparatus for edging and bevelling operations, prior to insertion into the spectacle frame.

This invention offers a way of overcoming the disadvantages of the existing art, by providing a simple, accurate device capable of determining and/or measuring monocular pupillary deviations in the eyes of a patient who is looking at a distant or close object; such a device may be used in combination with a photographic mensurator, in order to record either of these two forms of pupil deviation on a photograph.

This new device, to determine and/or measure the monocular pupillary deviations in a patient's eyes, comprises a cross-bar, carrying two adjustable reticles, to determine and/or measure the distance between the pupil of each eye and the plane of virtual symmetry of the patient's face, the said bar being formed of two casings which one move telescopically in relation to each other, and each of which contains a runner capable of moving inside it under the control of an outside regulating knob, and connected to a removable reticle-holder pin, each such telescopic casing further comprising a downward-pointing arm, held against the corresponding inside or outside surface of one of the arms of the spectacle frame worn by a patient by at least one spring exerting force on each casing, the said device being characterized by the fact that each casing comprises an internal extension which enables the two casings to fit telescopically inside each other, and which includes a supporting surface for one end of a compression spring, in such a way that the force of the spring causes the casings to move away from each other, and presses the downward arms against the inside surface of the spectacle arms.

The cross-bar is thereby accurately positioned in relation to the frame to which lenses are to be fitted, because the extension rests on the corresponding frame aperture, so that the oculist can adjust the reticles precisely, by bringing them into line with the patient's pupils while he is looking at either a distant or a close object, by means of a mirror device, as described in French patent No. 2 384 232 of Mar. 15, 1977, filed by the same applicant.

In another embodiment of the invention, each runner comprises a projecting element, which fits into one of the turns of the threads on a revolving shank inside the casing, connected to a knob, thereby allowing the position of the runner in the casing to be controlled. This projecting element takes the form of a tooth forming an integral part of the runner, to which it is connected by an elastic bracket, acting as torque limiter, so that the tooth can separate from the threading if the runner is jammed or pressing against another surface, and so that it can be reinserted into the threading by rotating the control knob.

In one particularly economical and attractive embodiment of the invention, each runner moves along the cross-bar in an internal groove, the cross-section of which is entirely surrounted by the casing, except for an opening at the bottom, to provide a passage for an extension of the runner, to which the reticle-holder pin is attached. The groove preferably has a polygonal cross-section, and the cross-section of the runner comprises surfaces in contact with each surface of the groove.

It will be easier to fit each runner inside its casing if the runner possesses a hollow rectangular cross-section, with a through shaped lower part, containing the bottom opening, and a lid-shaped upper part, glued, welded, screwed, or attached together in any other way, to complete the groove cross-section and enclose the runner inside the groove.

The downward-pointing arm of the runner may contain several holes into which a double-L shaped reticle-holder pin can be inserted from below, in order to bring the reticle closer to the centre of the cross-bar in relation to the runner. Each reticle may be oblong, and to it may be attached, by snap-on action a vertically sliding clip comprising two or three elastic arms, as well as a handle and a horizontal bar.

Figure 2:
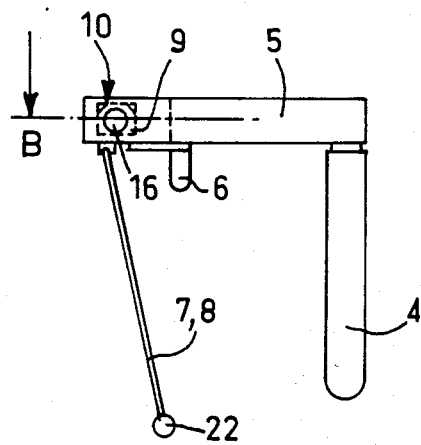
Figure 3:
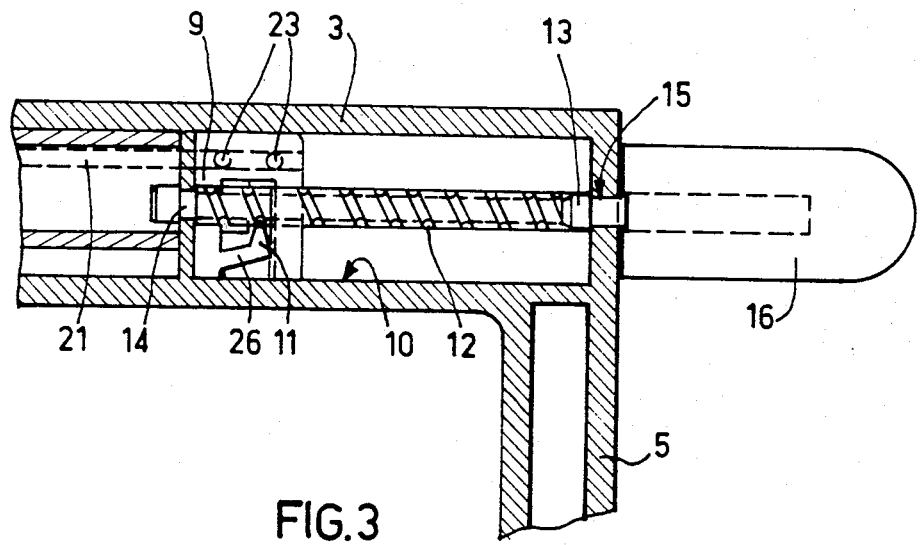
Figure 4:
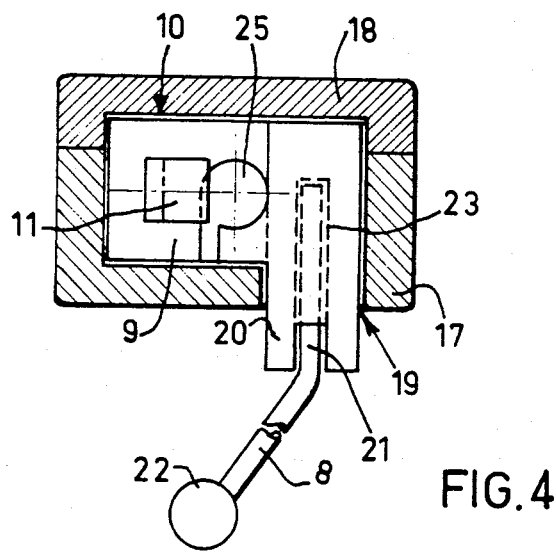
Figure 5:
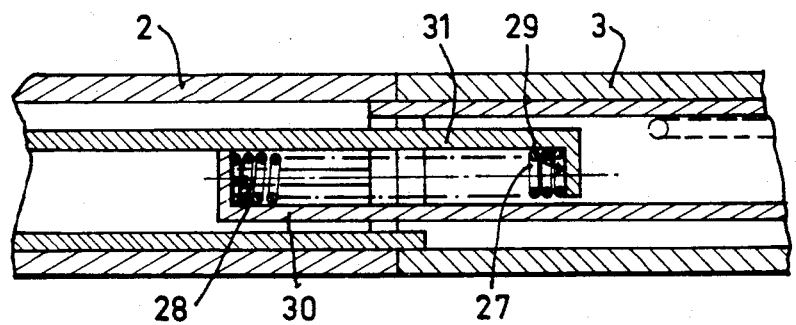
Figure 6A:
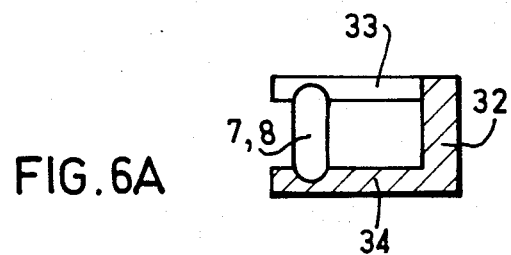
Figure 6B:
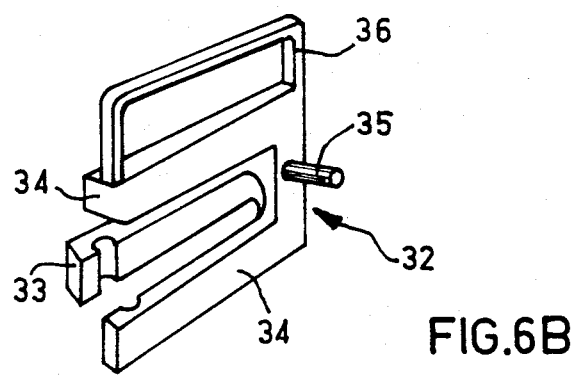

The following description of one possible embodiment of the invention will reveal other functions, features and advantages, with reference to the accompanying figures:

FIG. 1, showing the device from the front, comprising a cross-bar;

FIG. 2, showing a side view of the cross-bar and reticle;

FIG. 3, showing a cross-section of one end of the cross-bar, along plane B in FIG. 2;

FIG. 4, showing a cross-section of the cross-bar and of one of the runners along plane A of FIG. 1;

FIG. 5, showing a larger-scale partial cross-sectional view of the central part of the cross-bar when the device is retracted to minimum length;

FIGS. 6A and 6B, showing cross-sectional and perspective views of a clip comprising a horizontal bar, and designed to slide vertically on each reticle.

The device illustrated in FIG. 1 comprises a cross-bar 1, composed of two casings 2 and 3, which slide partly inside each other, so that the minimum and maximum distances between the downward-pointing arms 4 designed to rest on the surface of the arms of a spectacle frame are approximately 120 and 146 mm, thereby allowing it to be used with any size of frame.

The bottom of each casing 2 and 3 carries a short projecting portion 6, which rests on the top of the appropriate frame opening, so that the whole device can be fitted to the frame.

Two reticles 7 and 8, which are on a vertical plane when the device is placed on the spectacle frame, and at an angle on this plane, as shown in FIG. 2, to allow for the average angle of frames, are attached to two runners 9, which can slide inside grooves 10 provided for the purpose at the end of each casing.

In FIG. 5, a spring 27 in the middle of the cross-bar 1 pushes the two casings away from each other to the right distance, depending on the size of the spectacle frame. The ends of this spring rests on surfaces 28 and 29 on extensions 30 and 31 inside each casing. These extensions 30 and 31 enclose the spring 27 inside a cavity, formed together with the bearing surfaces 28 and 29. This spring 27 may be helical traction or compression spring, to push the two casings apart or draw them together, depending on whether the arms 4 rest on the outside or inside surface of the spectacle frame arms.

FIG. 3 shows the system of regulation of the sliding movement of each runner 9 inside the matching groove 10. In this system, a tooth-shaped projection 11 meshes with the thread 12 on a shank 13, which revolves on bearings 14 and 15 inside the casing 3, and is connected to a knob 16. This system is used to adjust the position of the runner 9 inside the casing 3. The knob projects beyond the edges 5 of the cross-bar 1, where it is easily accessible to the oculist.

The projecting tooth which fits into the threading 12 may be semicircular in section, and preferably forms an integral part of the runner 9, with which it is moulded in a single piece from a suitable material, such as plastic. The tooth is highly elastic, and acts as torque limiter when the runner 9 is in either of its end positions inside the groove 10. This prevents the runner from being jammed or blocked in either of these positions, which could damage the threaded shank 13. When the tooth has become separated from the thread, the shank 13 merely needs to be given a turn to readmit the tooth into the threading.

FIG. 4 shows a more detailed view of the inside groove 10 and corresponding runner 9. The groove, which has a rectangular overall cross-section, is made up of a trough-shaped lower part 17, and a lid-shaped upper part 18, fitted together in order to enclose the runner 9 inside the groove 10. The two parts 17 and 18 may be assembled by any method, for example by gluing or welding, when they are moulded from plastic. The runner 9 is entirely surrounded by the casing except, for an opening 19 in the bottom of the lower part 17, through which projects an extension 20 of the runner. A rod 21, carrying the reticle 7 or 8, surrounded by a ball 22 to prevent injuring the patient accidentally fits into this extension 20. This reticle-holder rod, which is double-L shaped, may be inserted into one of several openings 23 in the runner, as shown in FIG. 4. The runners contain surfaces in contact with each surface of the groove 10. A passage 25 inside each runner contains the threaded shank 13, which meshes with the tooth 11, supported by an elastic bracket 26, and forming an integral part of the runner 9.

FIG. 6A shows a reticle 7 or 8, which preferably has an oblong cross-section, and to which is attached, by snap-on action, a clip 32, with two or three elastic arms 33 and 34, allowing it to slide vertically on the reticle. FIG. 6B shows such a clip in perspective. It is provided here with a handle 35 and a horizontal opening 36. When the clip is brought level with the patient's eye, and this horizontal opening is made to coincide with the pupil of the eye, vertical co-ordinates for the pupil can be obtained, in relation to the upper and/or lower portions of the spectacle frame opening.

The device described above functions as follows.

The cross-bar 1 is positioned on the spectacle frame worn by the patient, by placing the projections 6 against the corresponding spectacle frame, and allowing the casing 2 and 3 to slide telescopically until the arms 4 come into contact with the frame arms. The oculist then adjusts the reticles 7 and 8, by turning the corresponding knobs 16, which cause the runner 9 to move along inside the groove 10, through the connection between the tooth 11 and the threaded shank 13, until each reticle coincides with the appropriate pupil of the patient's eye. When each reticle has been set to measure monocular pupillary deviations in near sight, and each horizontal opening 36 has been set by sliding the clip 32 vertically on the reticle, the oculist places a photographic mensurator opposite the patient, and asks him to look at a distant object, such as an infinite point produced by the mensurator, then takes the photograph. This photograph will show, in addition to the spectacle frame, the patient's pupils in the far sight position, and two vertical images of the reticles, showing each monocular deviation in near sight, and two horizontal lines reproducing the horizontal openings 36, showing the vertical position of the pupils in near sight.

This new device can naturally be used on its own. The cross-bar 1 comprises a double measuring scale to left and right, each casing 2 and 3 being able to slide in relation to this scale, so that the originating point of the scale remains fixed, whatever the distance between the casing ends. In this embodiment, an indicator fixed to each carriage 9 and/or reticle 7 and 8 moves along the scale.

This invention is obviously not confined to the embodiments described and illustrated above: many variants are possible for someone skilled in the art, without any departure from the spirit of the invention.

What is claimed is:

1. A device to determine and/or measure the monocular pupillary deviations in a patient's eyes, comprising a cross-bar, carrying two adjustable reticles, to determine and/or measure the distance between the pupil of each eye, the said cross-bar being formed of two casings which can move telescopically in relation to each other, and each of which contains a runner capable of moving inside it under the control of an outside regulating knob, said runner being connected to a removable reticle-holder rod, each such telescopic casing futher comprising a downward-pointing arm, adapted to be held against the corresponding inside or outside surface of one of the arms of a spectacle frame worn by a patient by at least one spring exerting force on each casing, the said device being characterized by the fact that each casing comprises an internal extension which enables the two casings to fit telescopically inside each other, said internal extension including a supporting surface for one end of a compression spring, positioned in such a way that the force of the spring causes the casings to move away from each other, and presses the downward arms against the inside surface of the spectacle arms.

2. A device as defined in claim 1, in which each runner comprises a projecting element which fits into one of the turns of the thread on a revolving shank, said revolving shank being inside the casing and connected to a knob, thereby allowing the position of the runner in the casing to be controlled.

3. A device as defined in claim 2, in which the projecting element is tooth-shaped, and forms an integral part of the runner, said projecting element being connected to said runner so that the tooth can separate from the threading if the runner is in an end position and is jammed or pressing against another surface thereat, and so that it can be reinserted into the threading by rotating the control knob.

4. A cevice as defined in any one of claims 1 to 3, in which each runner moves along the cross-bar in an internal groove, the cross-section of said groove being entirely surrounded by the casing, except for an opening at the bottom, said opening providing a passage for an extension arm of the runner, the reticle-holder rod being attached to said extension arm the device being characterized by the fact that the runner possesses a hollow rectangular cross-section, with a trough-shaped lower part containing the bottom opening, and a lid-shaped upper part secured to said trough-shaped lower part, to complete the groove cross-section and enclose the runner inside the groove.

5. A device as defined in claim 4, in which the downward-pointing arm on the runner contains several holes, into which a reticle holder rod may be inserted from below, in order to bring the reticle closer to the centre of the cross-bar in relation to the runner.

6. A device as defined in any one of claim 1, 2, 3 or 5 in which a vertically sliding clip comprising at least two elastic arms, as well as a handle and a horizontal opening, is attached to each reticle by snap-on action.

* * * * *